(12) United States Patent
Cho et al.

(10) Patent No.: US 7,504,082 B2
(45) Date of Patent: Mar. 17, 2009

(54) MAGNETIC NANOPARTICLES COMPRISING GADOLINIUM AND METHOD OF FABRICATION

(75) Inventors: Hui-Ju Cho, Lugang Township, Changhua County (TW); Sheng-Ming Shih, Taipei (TW); Yuh-Jiuan Lin, Taishan Township, Taipei County (TW); Hong-Dun Lin, Taipei (TW); Kang-Ping Lin, Jungli (TW)

(73) Assignee: Industrial Technology Research institute, Hsinchu (TW)

( * ) Notice: Subject to any disclaimer, the term of this patent is extended or adjusted under 35 U.S.C. 154(b) by 170 days.

(21) Appl. No.: 11/336,347

(22) Filed: Jan. 20, 2006

(65) Prior Publication Data

US 2006/0120964 A1    Jun. 8, 2006

Related U.S. Application Data

(63) Continuation-in-part of application No. 10/741,238, filed on Dec. 19, 2003, now abandoned.

(30) Foreign Application Priority Data

Jul. 31, 2003    (TW) .............................. 92120948 A

(51) Int. Cl.
  *B32B 5/16*    (2006.01)
  *C01F 17/00*    (2006.01)
  *C01G 1/02*    (2006.01)

(52) U.S. Cl. ....................... 423/263; 423/632; 428/402; 977/777; 977/904; 977/915

(58) Field of Classification Search ................ 977/777, 977/895, 904, 915; 420/83, 416; 423/263, 423/632; 428/402
See application file for complete search history.

(56) References Cited

U.S. PATENT DOCUMENTS

| | | | | |
|---|---|---|---|---|
| 5,427,767 | A * | 6/1995 | Kresse et al. | 424/9.32 |
| 6,203,768 | B1 * | 3/2001 | McCormick et al. | 423/1 |
| 6,482,387 | B1 * | 11/2002 | Gulgun et al. | 423/593.1 |
| 6,797,380 | B2 * | 9/2004 | Bonitatebus et al. | 428/842.2 |
| 6,835,521 | B2 * | 12/2004 | Tsuji et al. | 430/137.17 |

OTHER PUBLICATIONS

Haik, Magnetic Nanoparticles for Self-Controlled Hyperthermia, Apr. 2006.*
Geller, "Crystal Structure of Gadolinium Orthoferrite, GdFeO3", The Journal of Chemical Physics, vol. 24, No. 6, Jun. 1956, 1236-1239.*

* cited by examiner

*Primary Examiner*—H. (Holly) T Le
(74) *Attorney, Agent, or Firm*—Thomas, Kayden, Horstemeyer & Risley

(57) ABSTRACT

Magnetic nanoparticles are applicable in imaging, diagnosis, therapy, and biomaterial separation. The magnetic nanoparticles are represented as $(Fe_wGd_x)_vZ_y$, wherein w is from 99.9% to 97.5%, x is from 0.1% to 2.5%, Z is an element of the group VIa, and v, y are positive numbers.

10 Claims, 18 Drawing Sheets

$Gd^{3+}/(Gd^{3+}+Fe^{2+}+Fe^{3+})= 0\ mole\%$ $Gd^{3+}/(Gd^{3+}+Fe^{2+}+Fe^{3+})= 0$ mole%

$Gd^{3+}/(Gd^{3+}+Fe^{2+}+Fe^{3+})= 2.46$ mole%

$Gd^{3+}/(Gd^{3+}+Fe^{2+}+Fe^{3+})$ = 3.33 mole%

$Gd^{3+}/(Gd^{3+}+Fe^{2+}+Fe^{3+})$ = 6.67 mole%

$Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor $Gd^{3+}/(Gd^{3+}+Fe^{3+}+Fe^{2+})$ (mol%) in precursor

MAGNETIC NANOPARTICLES COMPRISING GADOLINIUM AND METHOD OF FABRICATION

CROSS-REFERENCE TO RELATED APPLICATION

This application is a continuation-in-part (CIP) of U.S. application Ser. No. 10/741,238, now abandoned, filed Dec. 19, 2003, which claims the benefit of Taiwanese Application No. 92120948, filed Jul. 31, 2003.

BACKGROUND OF THE INVENTION

1. Field of the Invention

The present invention relates to magnetic nanoparticles applicable in imaging, diagnosis, therapy and biomaterial separation, and more particularly to magnetic nanoparticles suitable for use as contrast agents in Magnetic Resonance Imaging and a fabrication method thereof.

2. Description of the Related Art

In the biotechnology field, magnetic nanoparticles are applicable in imaging, diagnosis, therapy, biomaterial separation and so on. It is used, for example, in imaging as a contrast agent or a tracer to enhance the imaging contrast or to trace the presence of a certain disease. Furthermore, magnetic nanoparticles are also applicable in drug delivery and cancer therapy.

Currently, a number of image analysis techniques such as Computer Topography (CT), Magnetic Resonance Imaging (MRI), and ultrasound (US) are applied in disease diagnosis. The popular analysis technique of computer topography employs an X-ray to image for example, a human body by X-ray diffraction of various tissues with various densities. In addition, a contrast agent may be added during analysis to enhance the contrast among different tissues or organs. However, the radiation of X-rays may bring undesired side effects, thus Magnetic Resonance Imaging (MRI) has been provided as an alternative analysis technique.

Magnetic resonance imaging is capable of showing selectively image several different characteristics of tissues. The level of tissue magnetization at specific signal recording times during the MR imaging cycle generally determines the brightness of a particular tissue in the MRI images. Contrast is produced when tissues do not have the same level of magnetization. There are three primary magnetic characteristics of tissue that are the source of image contrast. Two of these are associated with the longitudinal magnetization. They are proton density and T1, the longitudinal relaxation time. The third characteristic is associated with the transverse magnetization. It is T2, the transverse relaxation time.

Diagnosis of brain disorders has been markedly improved by using MRI, which can delineate detailed anatomic structures with excellent tissue contrast on T1, T2, and proton density-weighted images; however, the inherent tissue characteristics do not always produce adequate contrast for some clinical applications. The administer materials that will alter the magnetic characteristics within specific tissues or anatomical regions, and can disclose abnormal enhancement after intravenous administration of contrast agents due to brain-blood-barrier (BBB) disruption. Advanced MR imaging technique, which can detect in vivo physiological changes in human brain, such as water diffusion, blood volume and blood flow have been implemented in clinical MR scanners.

Certain materials are susceptible to magnetic field and become magnetized when located in field. The orbital electrons in the atom rather than magnetic properties of the nucleus determine the susceptibility of a material. Contrast agents used in MRI are generally based on susceptibility effects. Using dynamic susceptibility contrast technique takes the advantage of T2 signal changes during the first-pass of a bolus of contrast agents. Hemodynamic parameters can then be calculated in terms of cerebral blood volume (CBV), cerebral blood flow (CBF) and mean transit time (MTT) for diagnosis in clinical.

MRI provides a non-invasive diagnosis. An MRI with contrast agent enhancement increases sensitivity and specificity of imaging in many cases particularly when relaxation times among different tissues are similar.

MRI contrast agents can be classified differently according to their magnetic properties (paramagnetic, ferromagnetic or superparamagnetic). However, current commercial MRI contrast agents employing magnetic nanoparticles have poor specificity and their contrast enhancement could be improved.

U.S. Pat. No. 5,427,767 discloses iron oxide doped with isotope including $^{155}$Gd, $^{156}$Gd, or $^{157}$Gd in. Pure isotope, however, costs much higher than a nature isotope mixture. Further, the doping ratio and its effect of improving magnetization or transverse relaxivity (r2) are not discussed.

SUMMARY OF THE INVENTION

Accordingly, an object of the present invention is to provide magnetic nanoparticles, applicable in imaging, diagnosis, therapy, biomaterial separation, thereby furthering development of its application as an MRI contrast agent.

Therefore, by utilizing magnetic nanoparticles with Gd or forming an outer shell of Gd or its compound around the magnetic nanoparticles, the invention provides magnetic nanoparticles. The magnetic nanoparticles can be selectively modified by at least one molecule (such as liposome, polymer, aliphatic compound or aromatic compound), or further react with at least one substance having specificity (such as an antibody, protein, peptide, enzyme, carbohydrate, glycoprotein, nucleotide or lipid) to form contrast agents or tracers with specificity. Furthermore, the magnetic nanoparticles having specificity can perform a specific therapy such as killing cancer cells without harming healthy cells after entering the patient by heat transferred from the external magnetic field.

According to the invention, the provided magnetic nanoparticles are represented as $(Fe_wGd_x)_vZ_y$, wherein w is from 0.999 to 0.975, x is from 0.001 to 0.025, Z is an element of the group VIa, and v, y are positive numbers.

The invention also provides a method of fabricating Gd-including iron oxide nanoparticles, comprising: (a) charging Gd and Fe ion salts in deionized water to form a mixture; (b) adjusting the pH value of the mixture to form precipitates.

The invention further provides a magnetic nanoparticle represented as $Fe_xM^a_vZ_y$, wherein Z is an element of the group VIa, x is greater, or equal to 0, and v, y are positive numbers, $M^a$ is an inner-transition element other than Gd.

DESCRIPTION OF THE DRAWINGS

The present invention can be more fully understood by reading the subsequent detailed description and examples with references made to the accompanying drawings, wherein.

DETAILED DESCRIPTION OF THE INVENTION

Figure 1:
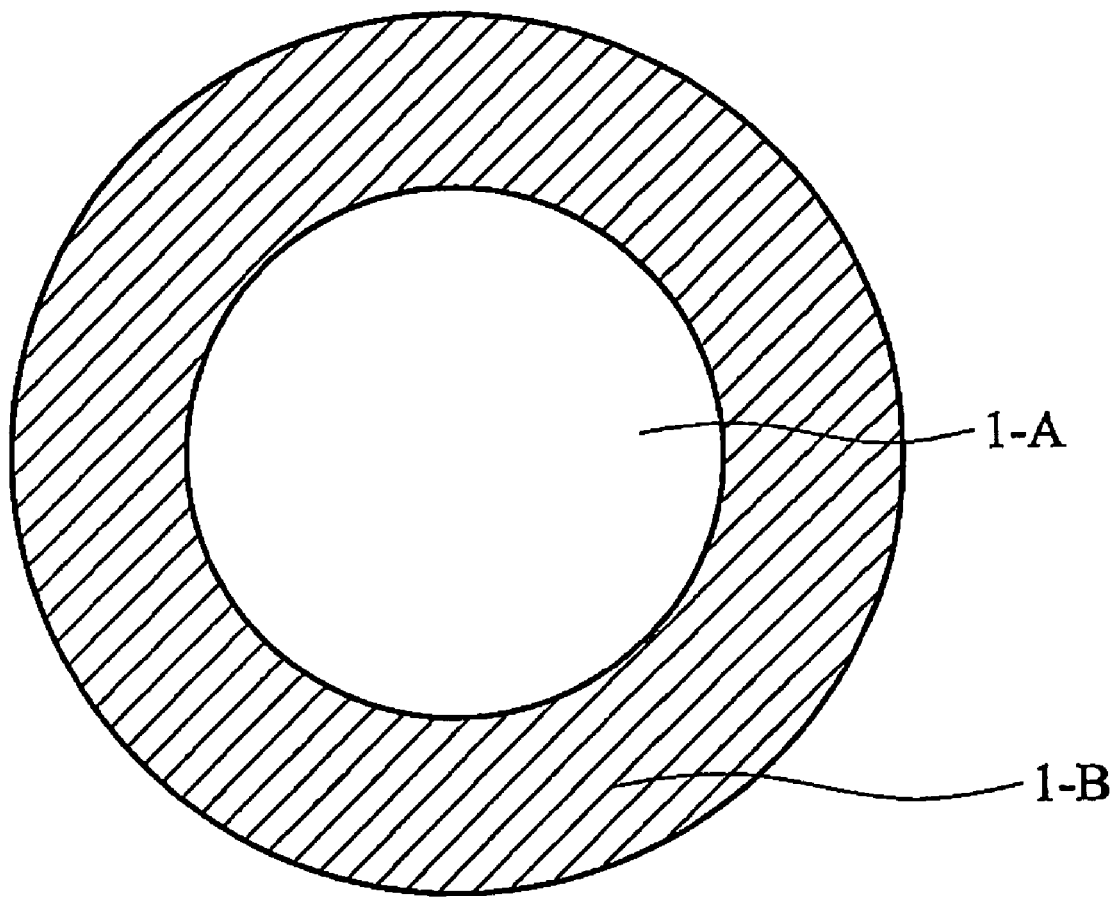
FIG. 1 illustrates the core-shell structure of magnetic nanoparticles of the invention.
Figure 2A:
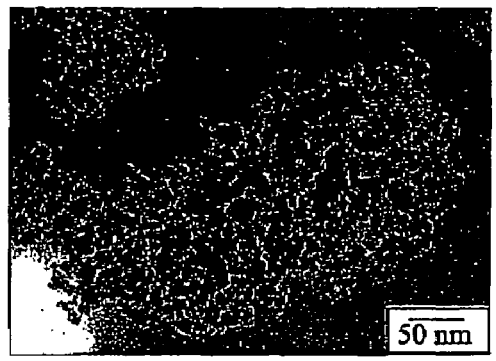
FIGS. 2a-2d show the magnetic nanoparticles prepared in air by Transmission Electron Microscope (TEM) observation.
Figure 2B:
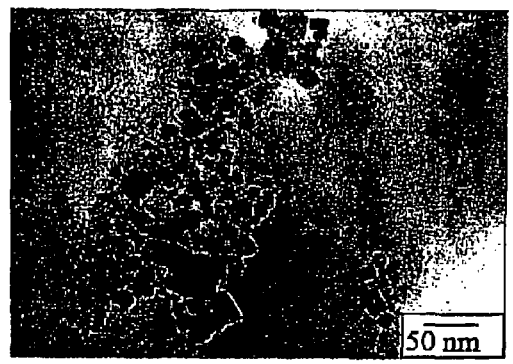
Figure 2C:
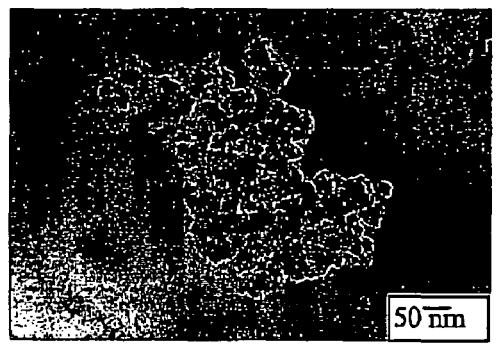
Figure 2D:
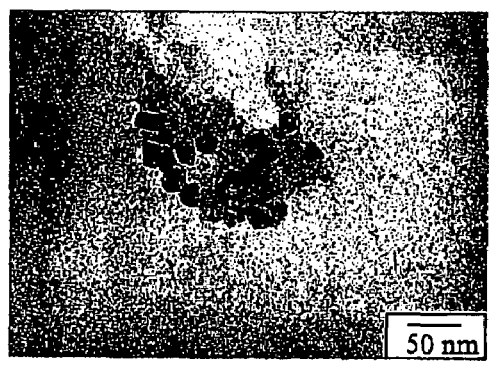

According to the invention, the provided magnetic nanoparticles may further have a core-shell structure as shown in FIG. 1, in which the core 1-A is represented as $Fe_xM^a_vZ_y$ while the shell 1-B is made of an inner-transition element $M^b$ or the compound thereof. Similarly, $M^a$ is an inner-transition element, Z is an element of the group VIa, x is greater than or equal to 0, while v and y are positive numbers. $M^a$ and $M^b$ may be the same or different elements.

According to the invention, the element Z is, for example, oxygen or sulfur.

The invention also provides magnetic nanoparticles presented as $(Fe_wGd_x)_vZ_y$, wherein w is from 0.999 to 0.975, x is from 0.001 to 0.25, Z is an element of the group VIa, and v, y are positive numbers. In preferred embodiments, the magnetic nanoparticles may have a transverse relaxivity (r2) of about 300 to 600 (mM Fe·s)$^{-1}$.

The invention also provides a method of fabricating Gd-including iron oxide nanoparticles, comprising: (a) charging Gd and Fe ion salts in deionized water to form a mixture; and (b) adjusting the pH value of the mixture to form precipitates. When performed in air, in step (a) mixing ratio of Gd ion salt/(Gd ion salt+Fe ion salt) is about 0.1 to 99 mol %, preferably about 0.1 to 3 mol %, and more preferably about 2.5 mol %. When steps (a) and (b) are performed under inert gas, the method further comprising a step (c) oxidizing the precipitates in an acidic solution to form Gd-including iron oxide nanoparticles; and in step (a) mixing ratio of Gd ion salt/(Gd ion salt+Fe ion salt) is about 0.1 to 99.9 mol %, preferably about 2.5-10 mol %, and more preferably about 5 mol %. The resulting Gd-including iron oxide nanoparticles preferably have a transverse relaxivity (r2) of about 300 to 600 (mM Fe·s)$^{-1}$.

The invention further provides a magnetic nanoparticle represented as $Fe_xM^a_vZ_y$, wherein Z is an element of the group VIa, x is greater, or equal to 0, and v, y are positive numbers, $M^a$ is an inner-transition element other than Gd.

According to the invention, the magnetic nanoparticles can be further modified by at least one molecule, such as a liposome, polymer, aliphatic compound, aromatic compound or combinations thereof.

The modified magnetic nanoparticles may further react with at least one substance having specificity, such as an antibody, a protein, a peptide, an enzyme, a carbohydrate, a glycoprotein, a nucleotide or a lipid. In addition, the substances with specificity may directly react with the unmodified magnetic nanoparticles to give specificity thereto.

EMBODIMENT

In the embodiment, magnetic nanoparticles of iron oxide doped with Gadolinium were given as an example, and the compound of the Gadolinium can be an oxide, sulfide, selenide, telluride, or polonide of the Gadolinium.

Preparation of Gd-Including Iron Oxide Nanoparticles in Air

In the embodiment, Gd-including iron oxide nanoparticles were prepared in air as an MRI contrast agent.

First, a reaction flask was charged with $FeCl_2$ powders (0.0069 moles), $FeCl_3$ powders (0.0138 moles) and deionized water (30 ml). $FeCl_3$ powders were replaced by $GdCl_3$ in various ratios in other examples. NaOH with a concentration of 5 M was added to control the pH value of the mixture. The mixture was subjected to continuous stirring during the reaction till the mixture became basic solution (the pH value approached about 11.5). Afterward, the temperature of the mixture was raised to and remained at 65° C. for 10 minutes. After black precipitates were formed, they were washed by deionized water and adjusted to acidic state by glacial acetic acid. Finally, $H_2O_2$ (10 vol %) was gradually added until the end of the gaseous reaction, and was followed by a deionized water wash.

Characterization of Gd-Including Iron Oxide Nanoparticles

1. Transmission Electron Microscope (TEM)

The magnetic nanoparticles prepared in air were then observed by TEM (JOEL, 100CX II). FIGS. 2a-2d respectively show the magnetic nanoparticles with an initial $Gd^{3+}/(Gd^{3+}+Fe^{2+}+Fe^{3+})$ mixing ratio of 0, 2.46, 3.33 and 6.67 mol %. In these cases, their average diameters are about 8.2±1.6 nm, 14.6±2.7 nm, 19.6±3.2 nm and 22.1±3.5 nm, respectively. The diameter of the nanoparticles is in direct proportion to initial Gd mixing ratio.

2. X-Ray Diffraction (XRD)

Figure 3:
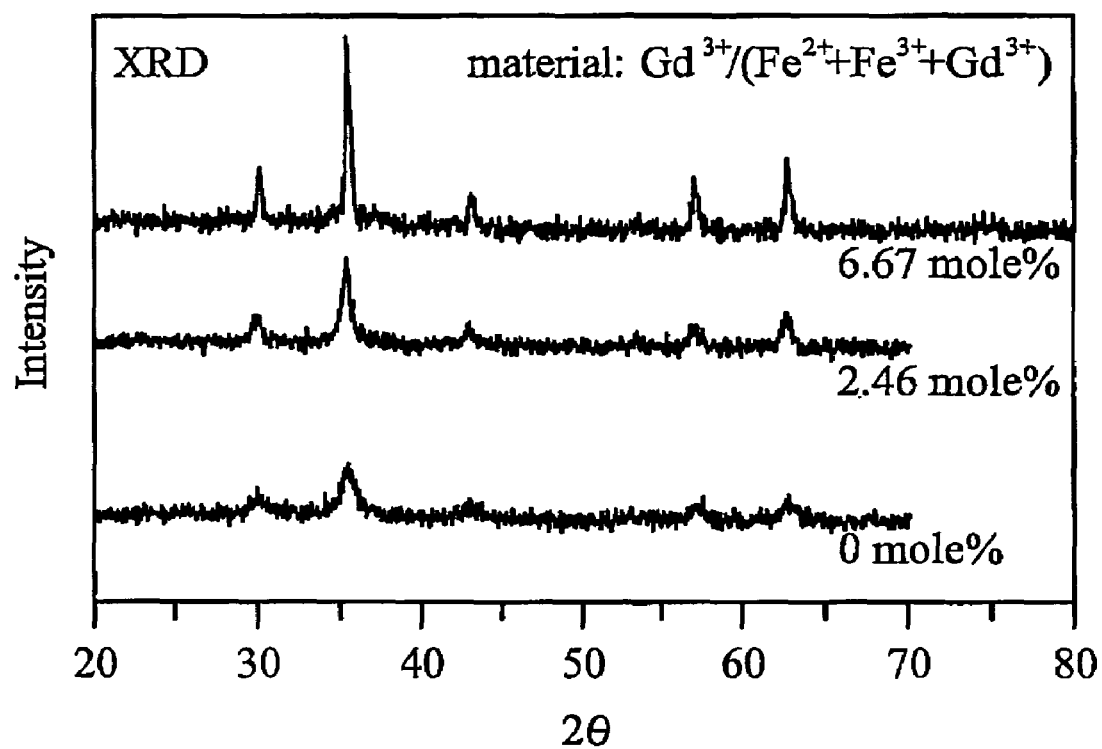
FIG. 3 shows the X-ray diffraction (XRD) analysis of the magnetic nanoparticles prepared in air.

FIG. 3 shows the XRD analysis of the magnetic nanoparticles prepared in air, further proving that the magnetic nanoparticles are iron oxide nanoparticles.

3. Inductively Coupled Plasma—Atomic Emission Spectrometry (ICP-AES)

Figure 4:
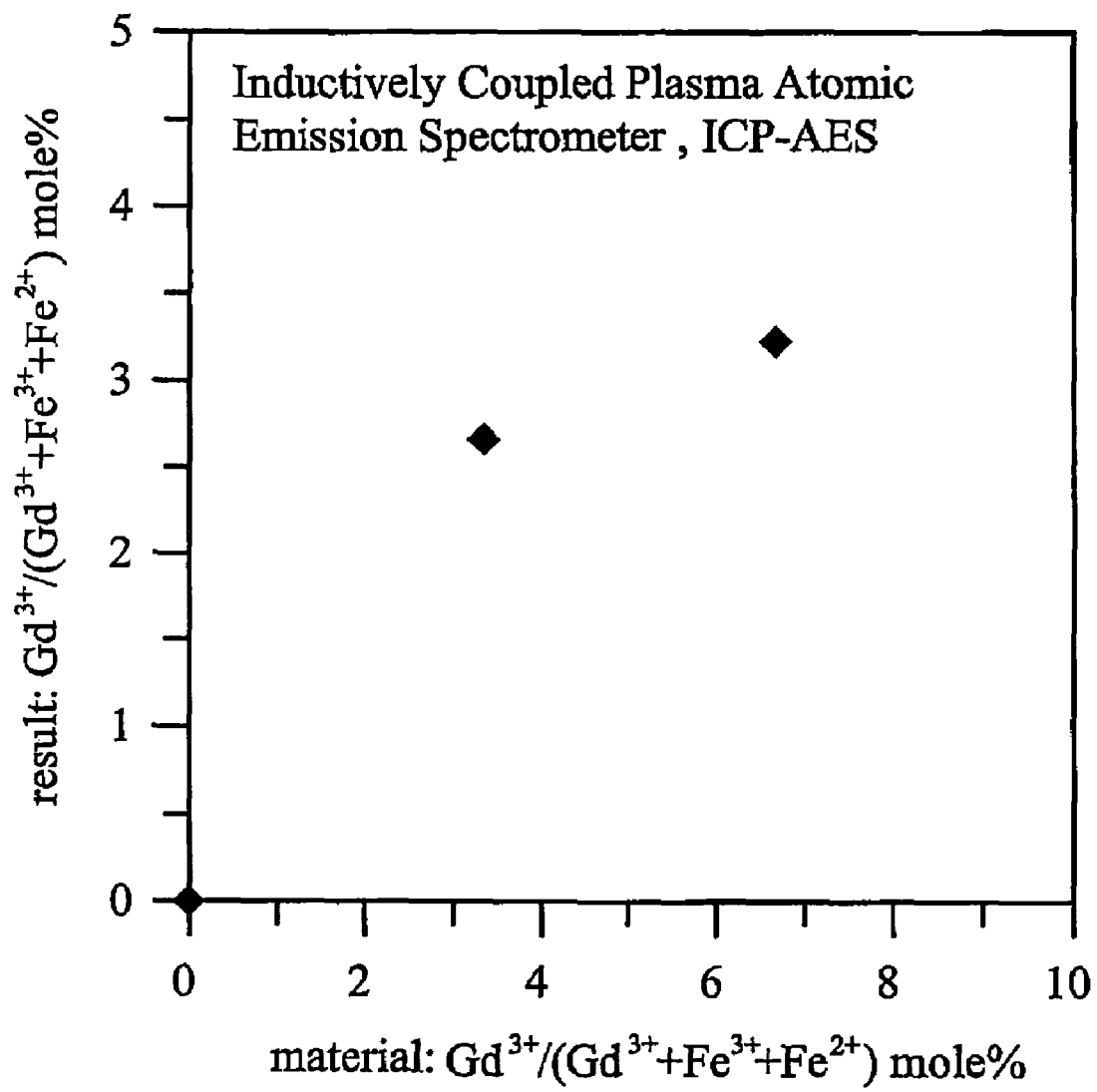
FIG. 4 shows the Inductively Coupled Plasma—Atomic Emission Spectrometry (ICP-AES) analysis of the magnetic nanoparticles prepared in air.

FIG. 4 shows the ICP-AES analysis of the magnetic nanoparticles prepared in air. The magnetic nanoparticles with an initial $Gd^{3+}/(Gd^{3+}+Fe^{2+}±Fe^{3+})$ mixing ratio of 0 mol %, 3.33 mol % or 6.67 mol % have a final $Gd^{3+}/(Gd^{3+}+Fe^{2+}+Fe^{3+})$ ratio in the nanoparticles of 0 mol %, 2.65 mol % or 3.20 mol %. The final Gd ratio is in direct proportion to the initial Gd mixing ratio.

4. Super-conducting Quantum Interference Device (SQUID)

Figure 5:
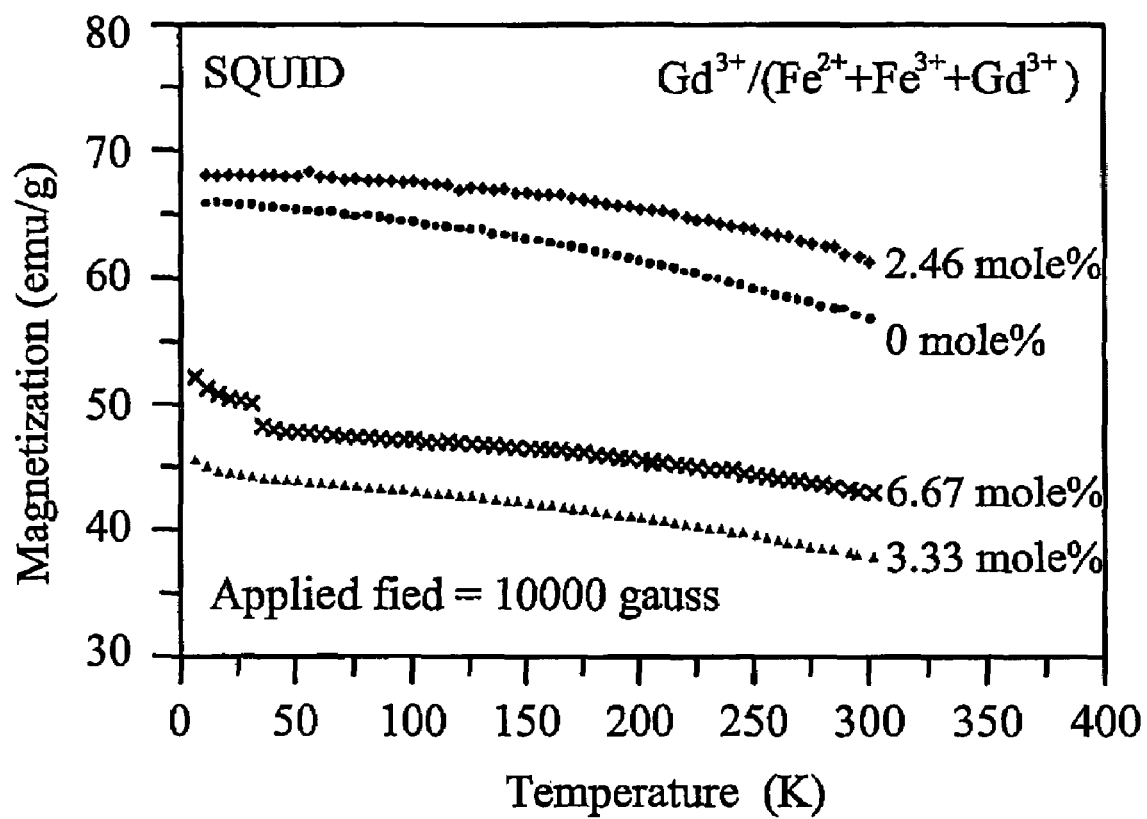
FIG. 5 shows the Super-conducting Quantum Interference Device (SQUID) analysis of the magnetic nanoparticles prepared in air.

FIG. 5 shows the SQUID analysis of the magnetic nanoparticles prepared in air. The results indicate a 3-8% increased magnetization of the magnetic nanoparticles having 2.46 mol % of initial Gd mixing ratio.

5. Magnetic Resonance Imaging (MRI)

Figure 6:
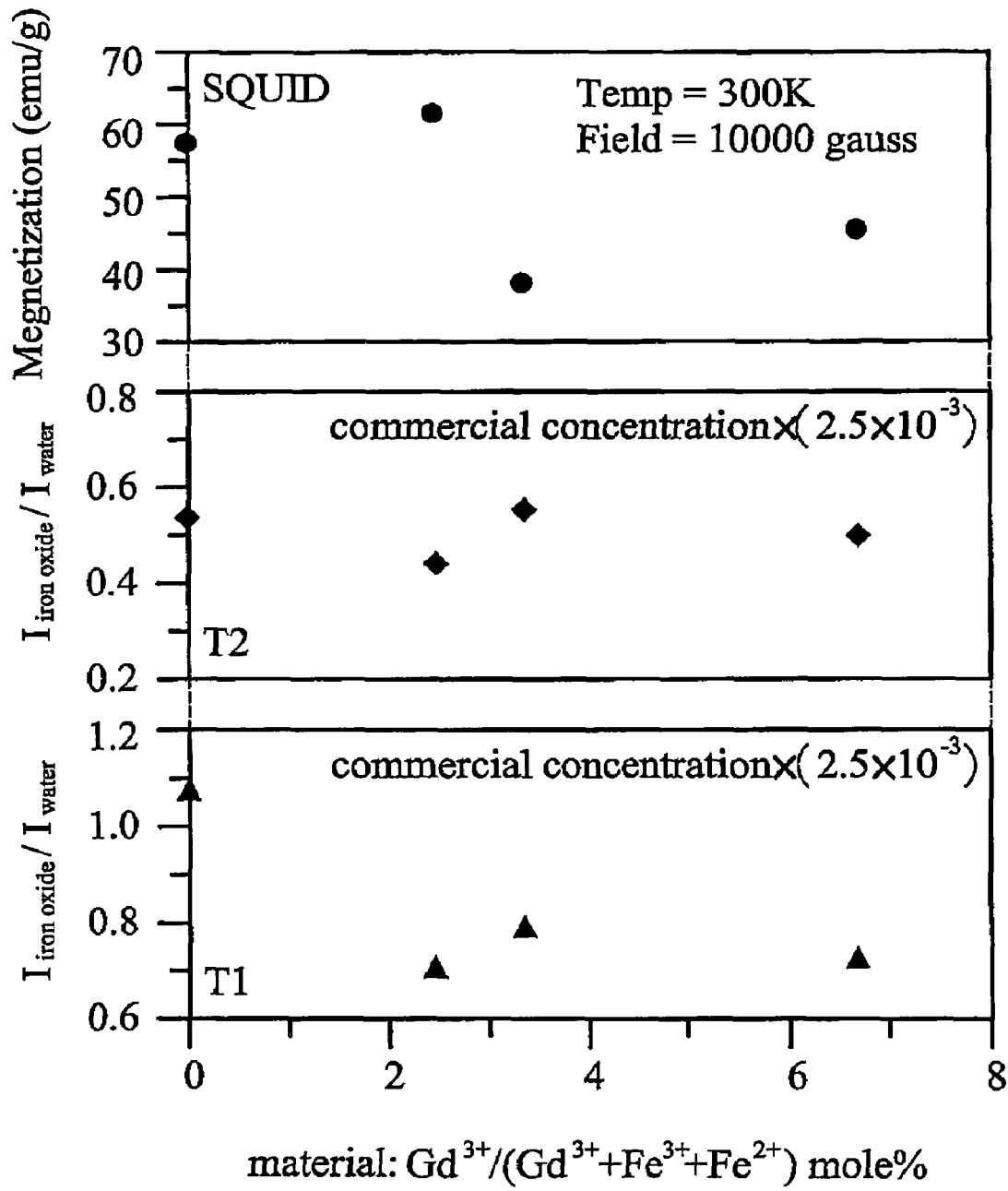
FIG. 6 shows the Magnetic Resonance Imaging (MRI) analysis of the magnetic nanoparticles prepared in air.
Figure 7A:
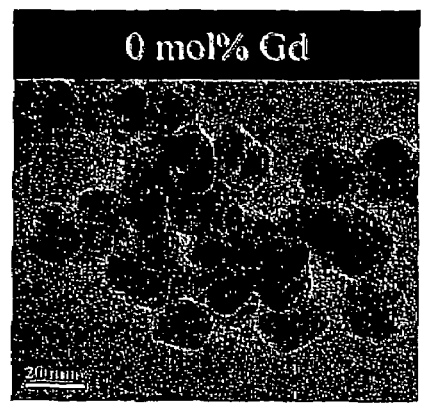
FIGS. 7a-7i show the magnetic nanoparticles prepared under argon by Transmission Electron Microscope (TEM) observation.
Figure 7B:
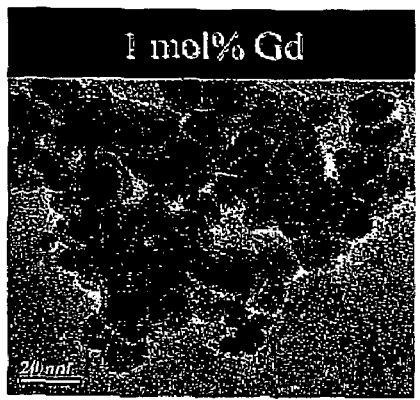
Figure 7C:
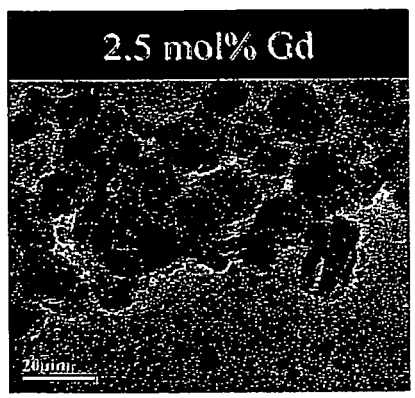
Figure 7D:
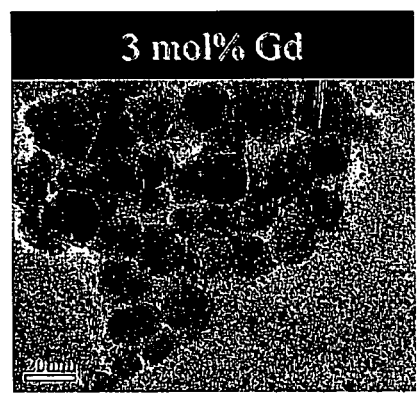
Figure 7E:
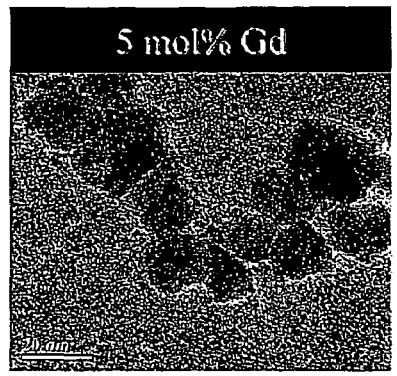
Figure 7F:
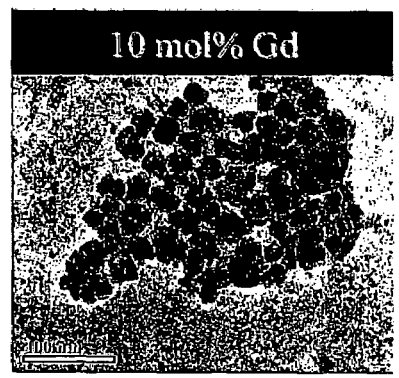
Figure 7G:
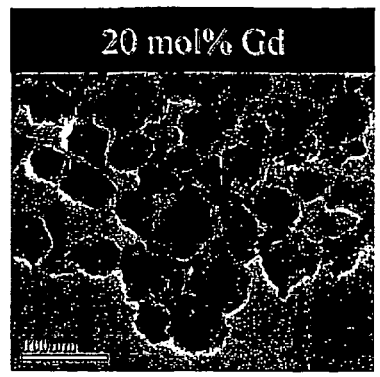
Figure 7H:
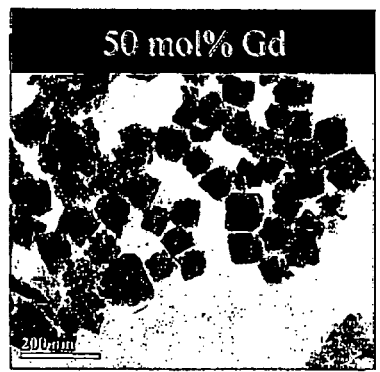
Figure 7I:
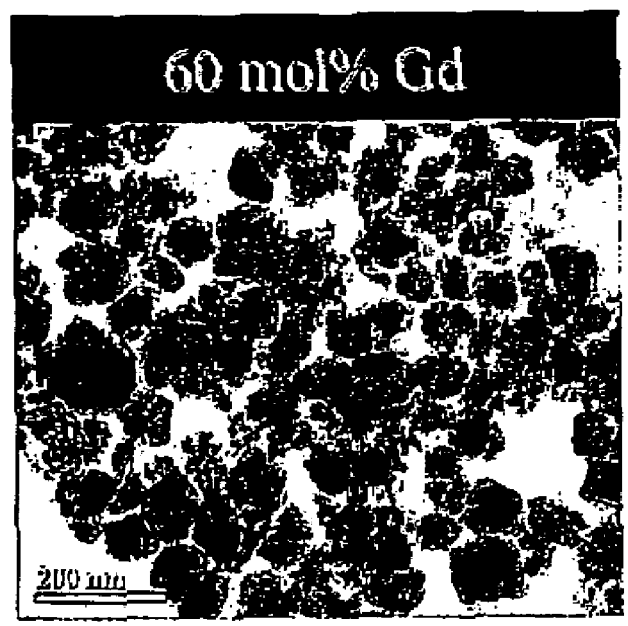

After clinically injecting a contrast agent, the concentration of the contrast agent is diluted by blood or body fluid, so the effective concentration is less than the concentration of the commercial contrast agent. Therefore, the provided magnetic nanoparticles were prepared as a contrast agent having a concentration $2.5\times10^{-3}$ times that of a commercial MRI iron oxide contrast agent. FIG. 6 shows the MRI analysis using the magnetic nanoparticles as a contrast agent. The longitudinal coordinates represent the signal intensity ratios of the oxides and water molecules. The greater the coordinates deviates from 1, the better the contrast enhancement is. As shown in FIG. 5, all of the four kinds of magnetic nanoparticles with various Gd initial mixing ratios exhibited contrast-enhancing capability. Especially, the iron oxide nanoparticles having 2.46 mol % additive $GdCl_3$ increased the contrast 18% more than that having non additive $GdCl_3$ under $T_2$-weignted conditions. Note that the contrast enhancement is not in direct proportion to the initial mixing ratio. To the contrary, the maximum enhancement is provided when the initial mixing ratio is about 0.1-3 mol % when prepared in air, particularly about 2.5 mol %.

Preparation of Gd-Including Iron Oxide Nanoparticles Under Inert Gas

In another embodiment, Gd-including iron oxide nanoparticles were prepared under inert gas as an MRI contrast agent.

Under argon atmosphere, a reaction flask was charged with $FeCl_2$ powders (0.0345 moles), $FeCl_3$ powders (0.069 moles) and deionized water (150 ml) $FeCl_3$ powders were replaced by $GdCl_3$ in various ratios. NaOH with a concentration of 5 M was added to control the pH value of the mixture. The mixture was subjected to continuous stirring during the reaction till the mixture became basic solution (the pH value approached about 11.5). Afterward, the temperature of the mixture was raised to and remained at 65° C. for 10 minutes. After black precipitates were formed, they were washed by deionized water and adjusted to acidic state by glacial acetic acid. Finally, $H_2O_2$ (10 vol %) was gradually added until the end of the gaseous reaction, and was followed by a deionized water wash. Note that before the precipitates were formed, all procedures were performed under argon.

The nanoparticles were dispersed in deionized water, dextran (Mw=10,000) is then added. After supersonic vibration, NH4OH was added to control the pH to 10. Continuously stirred, heated to 75☐ and stirred at 75☐ for 75 minutes. The suspension was dialyzed (using a membrane with molecular weight cutt off (MWCO) at 10,000) for removing excess dextran. The described suspension was put in a centrifuge at 6000 rpm for 30 minutes to remove the aggregates. Finally, the suspension is filtered over a filter of 0.2 μm in pore size to get surface modified nanoparticles.

Characterization of Gd-Including Iron Oxide Nanoparticles

1. Transmission Electron Microscope (TEM)

Figure 8:
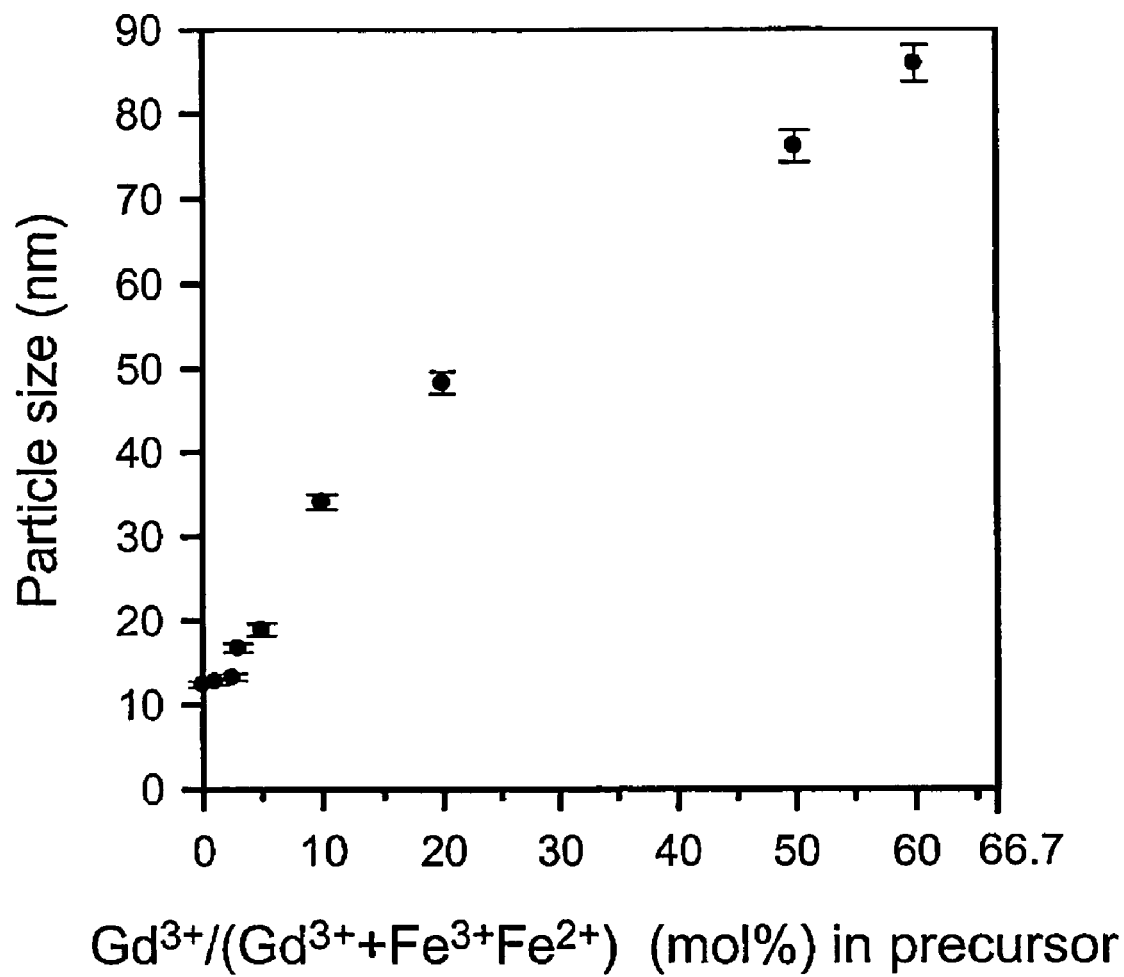
FIG. 8 shows particle size versus initial mixing ratio.

The magnetic nanoparticles were then observed by TEM (JOEL, 2010). FIGS. 7a-7i respectively show the magnetic nanoparticles with an initial $Gd^{3+}/(Gd^{3+}+Fe^{2+}+Fe^{3+})$ mixing ratio of 0, 1, 2.5, 3, 5, 10, 20, 50, and 60 mol %. In these cases, their average diameters are about 12.4±3.9 nm, 12.7±3.0 nm, 13.2±3.1 nm, 16.7±3.8 nm, 18.9±4.3 nm, 34.0±8.3 nm, 48.3±11.0 nm, 76.1±16.1 nm, and 85.9±22.2 nm, respectively. The diameter of the nanoparticles is in direct proportion to initial Gd mixing ratio, as shown in FIG. 8.

2. X-Ray Diffraction (XRD)

Figure 9:
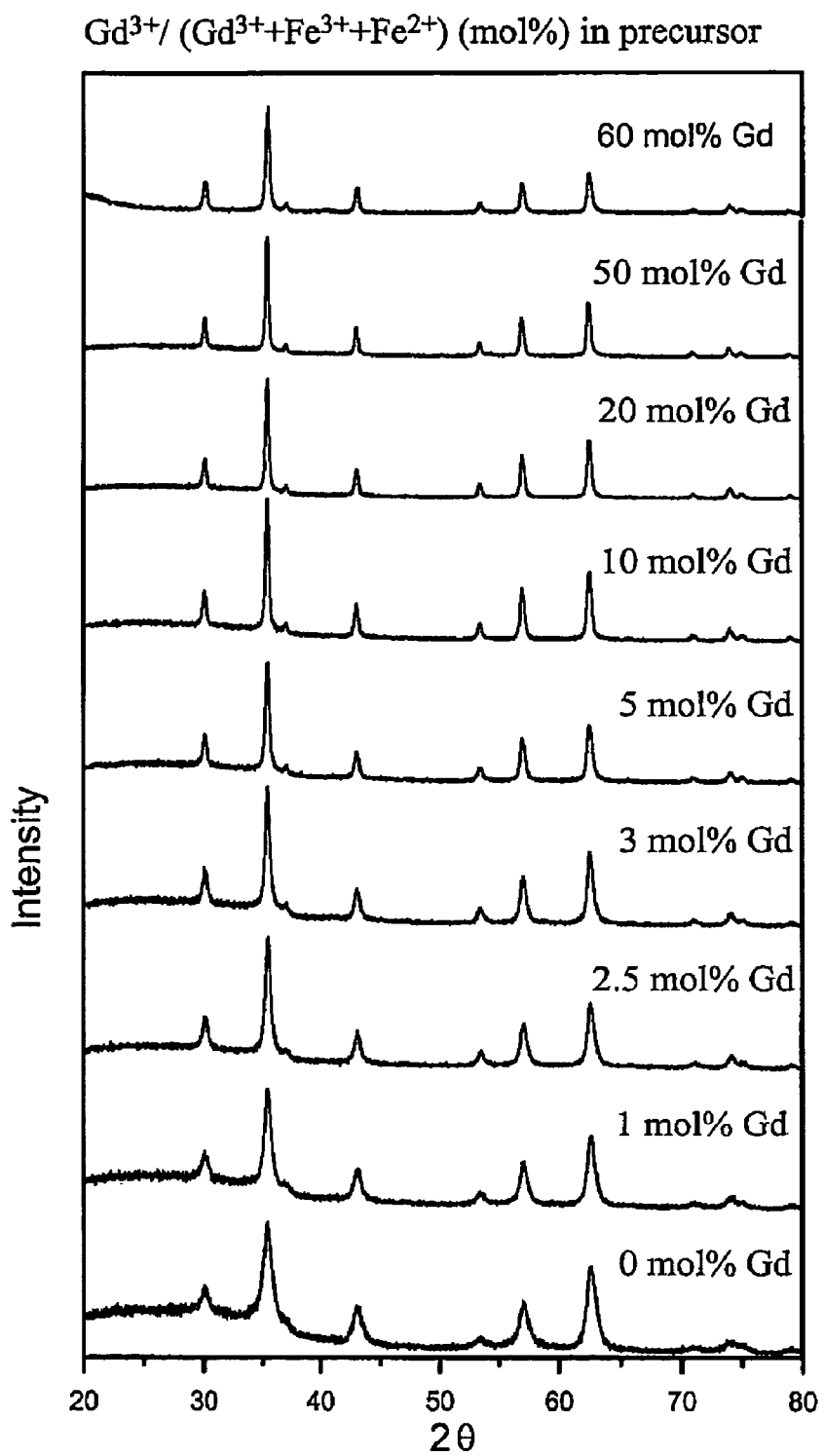
FIG. 9 shows the X-ray diffraction (XRD) analysis of the magnetic nanoparticles prepared under argon.

FIG. 9 shows the XRD analysis of the magnetic nanoparticles in the embodiment, further proving that the magnetic nanoparticles are iron oxide nanoparticles.

3. Inductively Coupled Plasma—Atomic Emission Spectrometry (ICP-AES)

Figure 10:
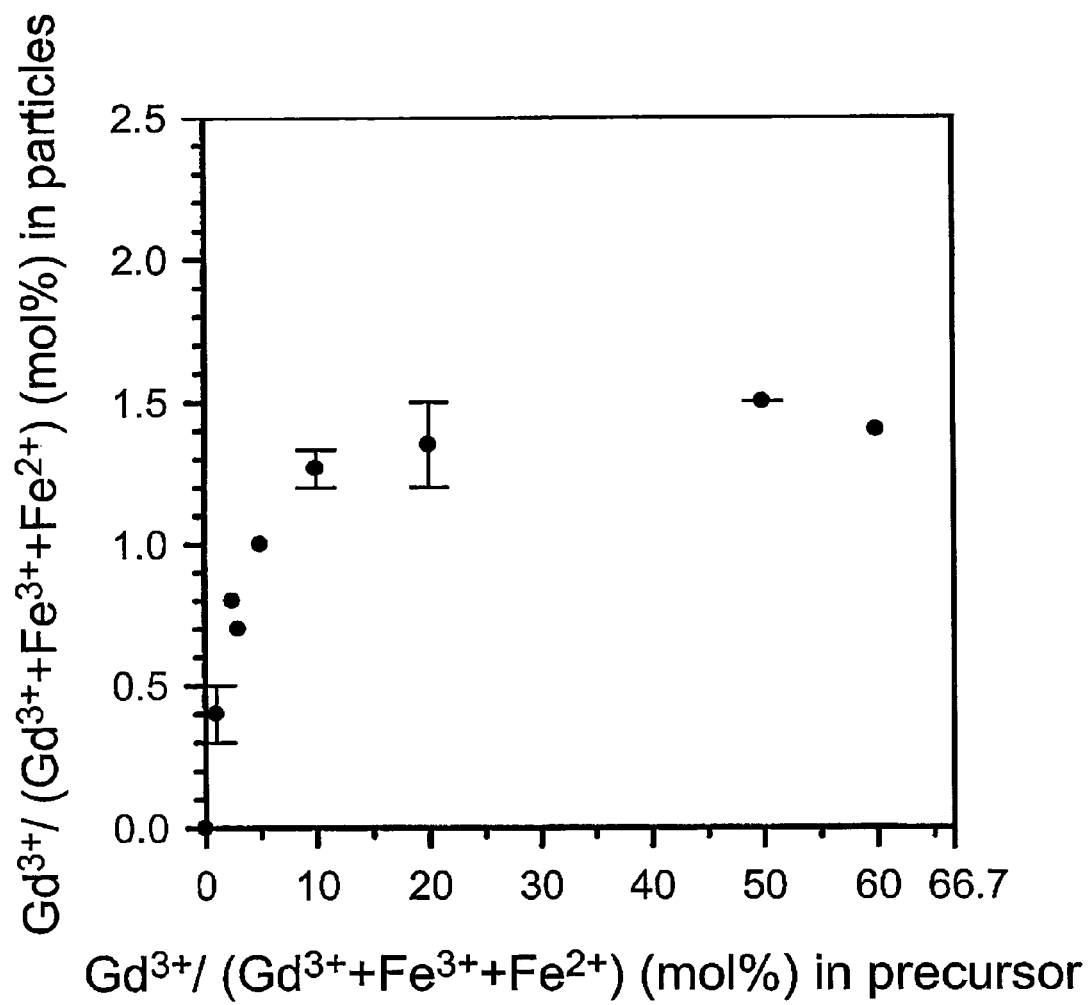
FIG. 10 shows the Inductively Coupled Plasma—Atomic Emission Spectrometry (ICP-AES) analysis of the magnetic nanoparticles prepared under argon.

FIG. 10 shows the ICP-AES analysis of the magnetic nanoparticles in the embodiment. The magnetic nanoparticles with an initial $Gd^{3+}/(Gd^{3+}+Fe^{2+}+Fe^{3+})$ mixing ratio of 0, 1, 2.5, 3, 5, 10, 20, 50, and 60 have a final $Gd^{3+}/(Gd^{3+}+Fe^{2+}+Fe^{3+})$ ratio in the nanoparticles of 0, 0.4±0.1, 0.8, 0.7, 1.0, 1.3±0.1, 1.4±0.1, 1.4±0.1, 1.5, and 1.4 mol %, respectively. Note that the final Gd ratio increases with the initial Gd mixing ratio before 20 mol %, but remains a constant after 20 mol %.

4. Super-conducting Quantum Interference Device (SQUID)

Figure 11:
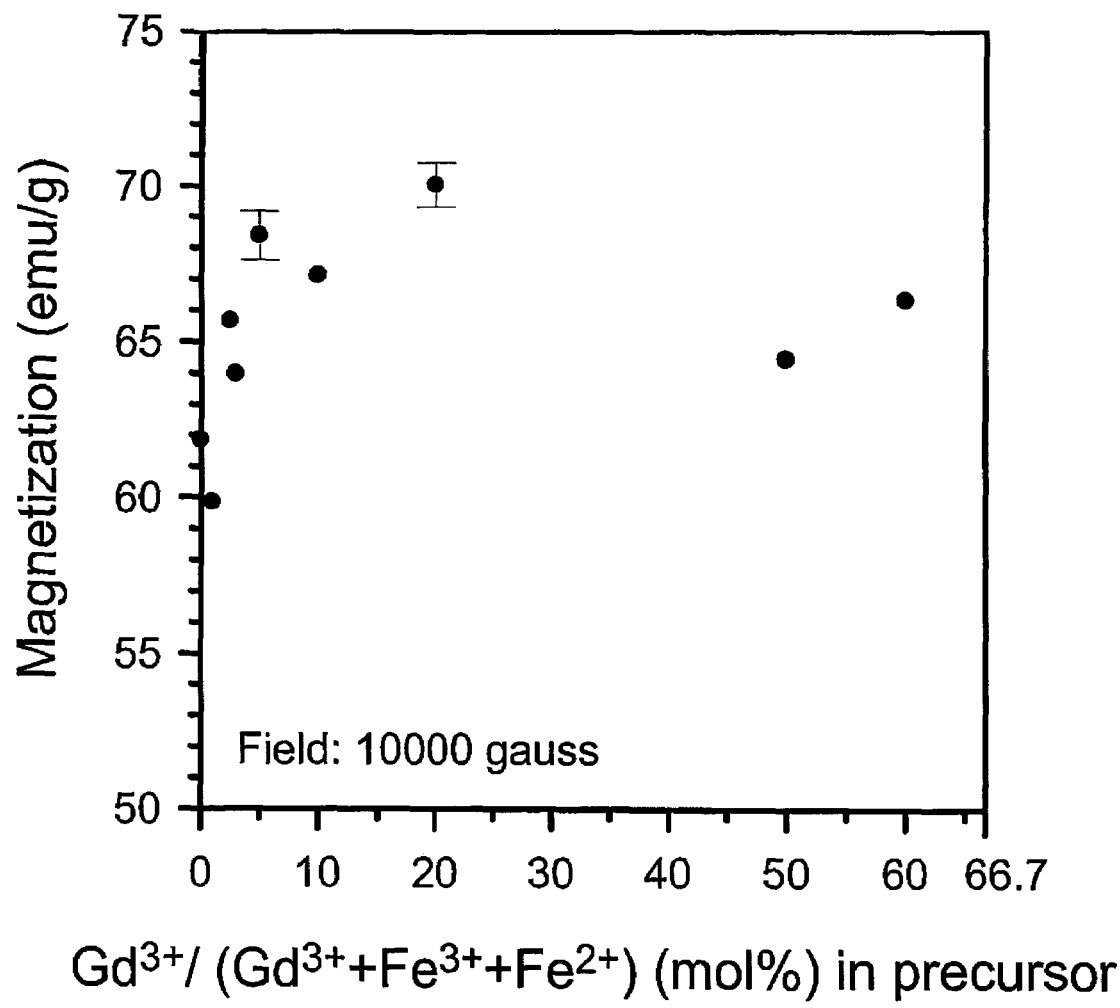
FIG. 11 shows the Super-conducting Quantum Interference Device (SQUID) analysis of the magnetic nanoparticles prepared under argon.

FIG. 11 shows the SQUID analysis of the magnetic nanoparticles in the embodiment. The results indicate a 13% increased magnetization of the magnetic nanoparticles having 20 mol % of $GdCl_3$ added.

5. Nuclear Magnetic Resonance (NMR)

Figure 12A:
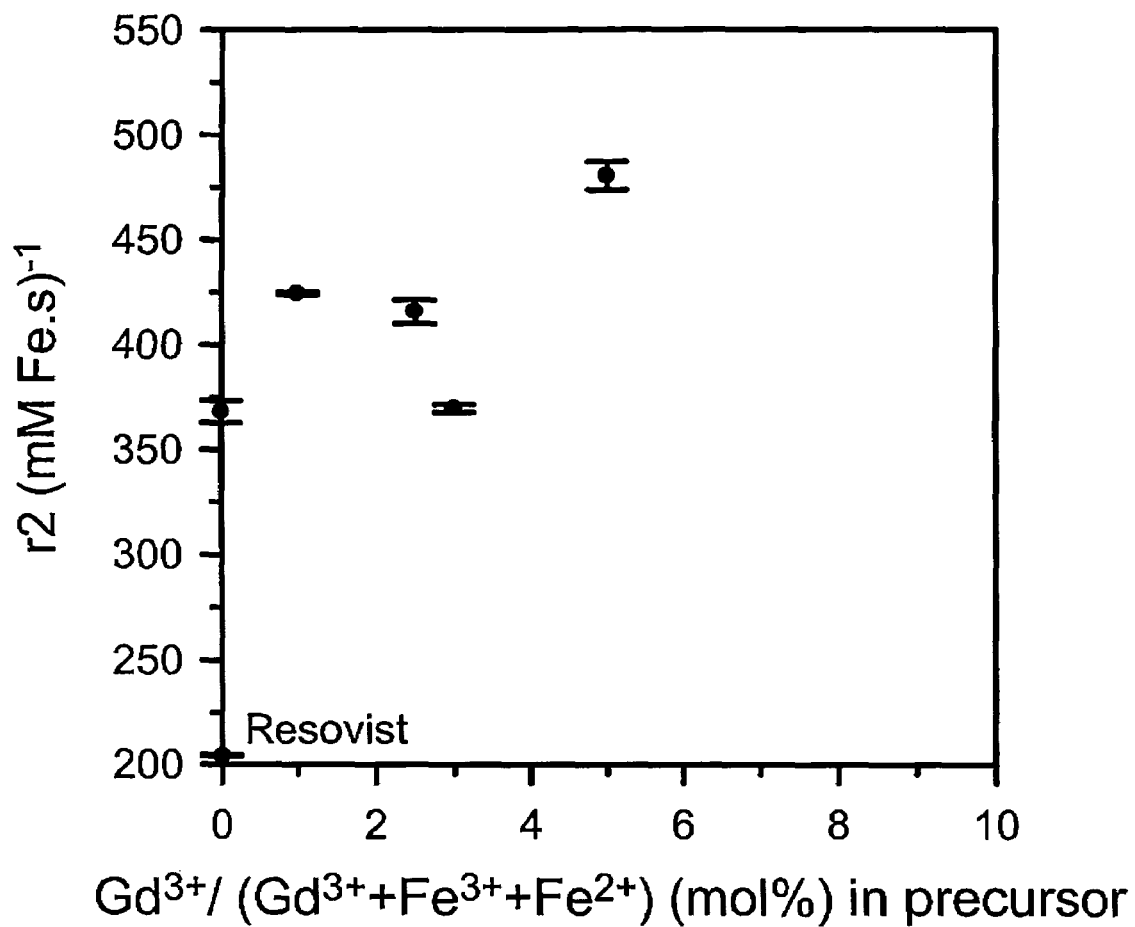
FIG. 12a-b shows the Nuclear Magnetic Resonance (NMR) analysis of the magnetic nanoparticles prepared under argon.
Figure 12B:
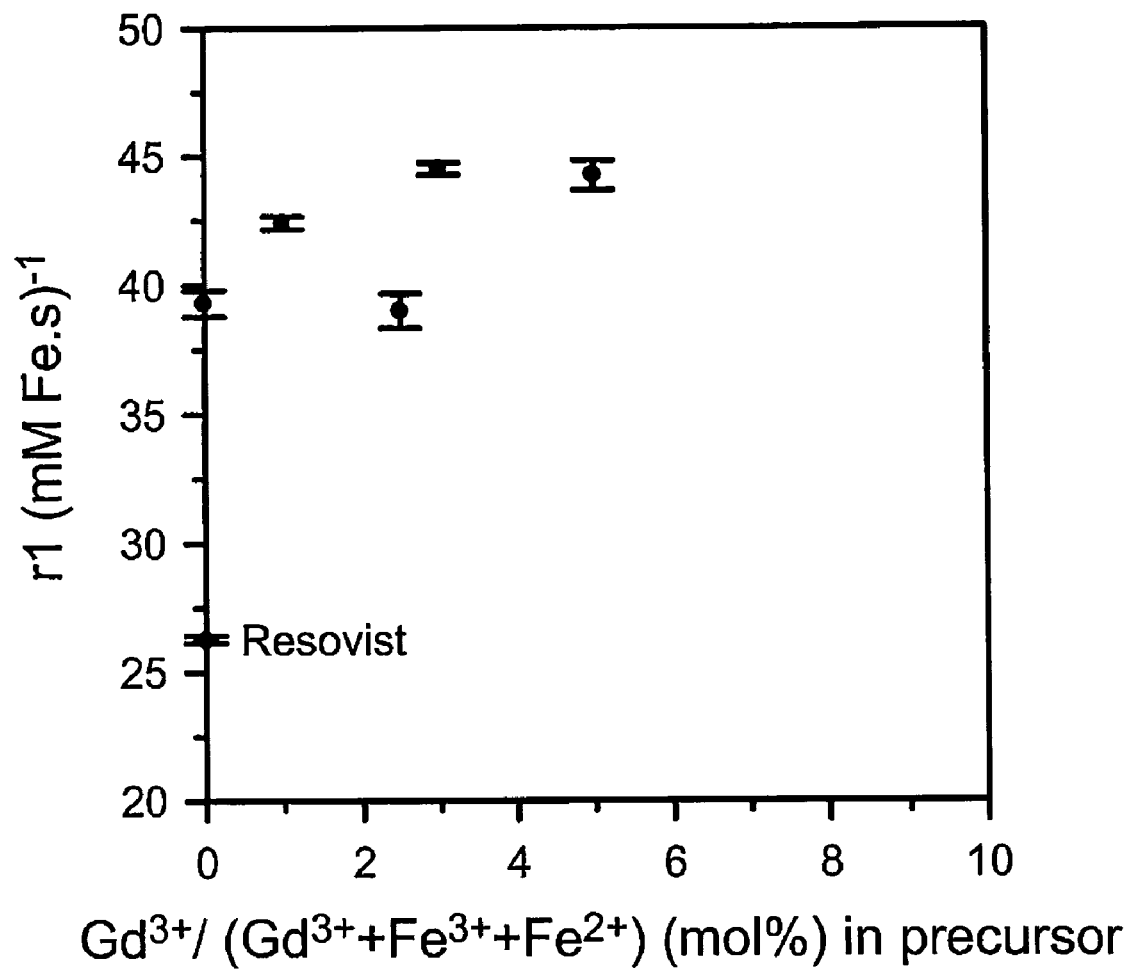

As shown in FIG. 12a, the magnetic nanoparticles which surface is modified by dextran with an initial $Gd^{3+}/(Gd^{3+}+Fe^{2+}+Fe^{3+})$ mixing ratio of 0, 1, 2.5, 3, and 5 mol % have a transverse relaxivity (r2) of 368±9, 424±1, 416±10, 370±3, and 480±12 (mM Fe·s)$^{-1}$, respectively. As shown in FIG. 12b, the magnetic nanoparticles with an initial $Gd^{3+}/(Gd^{3+}+Fe^{2+}+Fe^{3+})$ mixing ratio of 0, 1, 2.5, 3, and 5 mol % have a longitudinal relaxivity (r1) of 39.2±0.7, 42.4±0.4, 39.0±1.2, 44.5±0.4, and 44.2±1 (mM Fe·s)$^{-1}$. Note that commercial Resovist® has a transverse relaxivity of 204±1 (mM Fe·s)$^{-1}$, and a longitudinal relaxivity of 26.3±0.3 (mM Fe·s)$^{-1}$. Accordingly, the iron oxide nanoparticles having initial mixing ratio of 5 mol % additive $GdCl_3$ increased the r2 about 30% more than that having non additive $GdCl_3$. Compared to commercial Resovist®, the r2 is significantly increased by about 2.35 times.

Compared to U.S. Pat. No. 5,427,767, a cheaper natural isotope mixture is used instead of pure isotope. Furthermore, the invention provides a detailed discussion of doping procedure and the effects of doping ratio to contrast enhancement.

Accordingly, the Gd-including iron oxide nanoparticles enhance the contrast effectively and provide a clearer MRI image. Furthermore, the provided Gd-including iron oxide nanoparticles may be selectively modified by a molecule such as a liposome, polymer, aliphatic compound, or aromatic compound. The modified magnetic nanoparticles may further react with a substance having specificity, such as an antibody, a protein, a peptide, an enzyme, a carbohydrate, a glycoprotein, a nucleotide or a lipid to form a contrast agent having specificity.

The foregoing description has been presented for purposes of illustration and description. Obvious modifications or variations are possible in light of the above teaching. The embodiment was chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

What is claimed is:

1. Magnetic nanoparticles are presented as $(Fe_wGd_x)_vZ_y$, wherein Gd is naturally occurring Gd, w is from 0.999 to 0.975, x is from 0.001 to 0.025, Z is an element of the group VIa, and v, y are positive numbers.

2. The magnetic nanoparticles as claimed in claim 1, wherein the element Z is oxygen or sulfur.

3. The magnetic nanoparticles as claimed in claim 1, wherein the magnetic nanoparticles are applicable in imaging, diagnosis, therapy and biomaterial separation.

4. The magnetic nanoparticles as claimed in claim 1, further modified by at least one molecule.

5. The magnetic nanoparticles as claimed in claim 4, wherein the molecule is a liposome, polymer, aliphatic compound, aromatic compound or combinations thereof.

6. The magnetic nanoparticles as claimed in claim 4, wherein the magnetic nanoparticles further react with at least one substance having specificity.

7. The magnetic nanoparticles as claimed in claim 6, wherein the substance having specificity is an antibody, a protein, a peptide, an enzyme, a carbohydrate, a glycoprotein, a nucleotide or a lipid.

8. The magnetic nanoparticles as claimed in claim 1, wherein the magnetic nanoparticles further react with at least one substance having specificity.

9. The magnetic nanoparticles as claimed in claim 8, wherein the substance having specificity is an antibody, a protein, a peptide, an enzyme, a carbohydrate, a glycoprotein, a nucleotide or a lipid.

10. The magnetic nanoparticles as claimed in claim 1, wherein the magnetic nanoparticles have a transverse relaxivity (r2) of about 300 to 600 $(\text{mM Fe}\cdot\text{s})^{-1}$.

* * * * *